United States Patent [19]

Levy et al.

[11] 4,119,669

[45] Oct. 10, 1978

[54] 3,4-XYLIDINE COMPOUNDS WHICH ARE USEFUL AS HERBICIDES AND AS INTERMEDIATES IN THE PREPARATION OF 2,6-DINITRO-3,4-XYLIDINE HERBICIDES

[75] Inventors: Stephen David Levy; Robert Eugene Diehl, both of Trenton, N.J.

[73] Assignee: American Cyanamid Company, Stamford, Conn.

[21] Appl. No.: 560,847

[22] Filed: Mar. 21, 1975

Related U.S. Application Data

[63] Continuation of Ser. No. 373,079, Jun. 25, 1973, Pat. No. 3,920,742.

[51] Int. Cl.² .............. C07C 87/60; C07C 87/62; A01N 9/20

[52] U.S. Cl. .............................. 260/577; 71/121
[58] Field of Search .................. 260/577, 576; 71/121

[56] References Cited

U.S. PATENT DOCUMENTS 3,920,742  11/1975  Lutz et al. .............................. 260/577

*Primary Examiner*—Winston A. Douglas
*Assistant Examiner*—John J. Doll
*Attorney, Agent, or Firm*—Robert P. Raymond

[57] ABSTRACT

Novel N-alkyl-3,4-xylidine herbicides are disclosed, together with methods for their preparation and use for controlling undesirable plants by application of the xylidines to the foliage or soil containing the seeds thereof and are useful as intermediates in the preparation of 2,6-dinitro-3,4-xylidine herbicides.

1 Claim, No Drawings

3,4-XYLIDINE COMPOUNDS WHICH ARE USEFUL AS HERBICIDES AND AS INTERMEDIATES IN THE PREPARATION OF 2,6-DINITRO-3,4-XYLIDINE HERBICIDES

This is a continuation, of application Ser. No. 373,079, filed June 25, 1973, now U.S. Pat. No. 3,920,742, granted Nov. 18, 1975.

The present invention relates to certain novel N-alkyl-3,4-xylidines and to their use as herbicides directly or following nitration. It further relates to a process useful in their preparation and nitration.

The novel compounds of the present invention are illustrated by the formula:

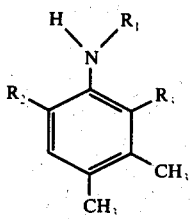

wherein $R_1$ represents a branched chain alkyl $C_4$–$C_5$ selected from the group of sec-butyl, 1-methylbutyl and 1-ethylpropyl and $R_2$ and $R_3$ each represent members selected from the group of hydrogen and nitro, with the proviso that $R_2$ and $R_3$ cannot both be nitro.

The present invention also concerns the use of certain of the formula I compounds to control undesirable plant species, namely, the mononitro compounds. They may be used to control a wide variety of undesirable monocotyledonous and dicotyledonous plants. They exhibit both preemergence and postemergence herbicidal activity and can be applied to foliage of the undesired plant or to the soil containing its seeds, preferably in solid or liquid formulations with a conventional horticultural adjuvant or formulation aid, such as a dispersing agent or surfactant.

Accordingly, the herbicidal method of the present invention comprises applying a herbicidally effective amount of a compound having formula I wherein $R_2$ or $R_3$ is nitro to the foliage of undesirable plant species or soil containing seeds of undesirable plant species. Control is usually achieved by applying one or more of the active ingredients at a rate of about 1 to 25 pounds per acre.

Solid formulations that can be used include dusts, dust concentrates and granular products. For application in liquid form, the product is usually first prepared as a wettable powder containing about 25% to 95% of the active compound, from about 4% to 70% by weight of a finely divided diluent such as kaolin, attapulgus clay, silica, pumice, talc or diatomaceous earth and from about 1% to 5% by weight of a dispersing agent such as an alkali metal salt of naphthalene sulfonic acid, alkali metal lignosulfonate or the like. The formulation may also contain from about 1% to 5% by weight of a surfactant such as sodium N-methyl-N-oleoyltaurate, alkyl phenoxypolyoxyethylene ethanol, sorbitan fatty acid ester or the like. The wettable powder is usually dispersed in water for application as a liquid spray.

In addition to and more important than their use as herbicides directly, the novel compounds of formula I have an unexpected advantageous utility as intermediates in the manufacture of N-sec-butyl-2,6-dinitro-3,4-xylidine; N-(1-ethyl-propyl)-2,6-dinitro-3,4-xylidine and N-(1-methylbutyl)-2,6-dinitro-3,4-xylidine, which relate to copending application Ser. No. 323,000, filed Jan. 12, 1973.

The process described in our copending application for preparing these dinitro compounds involved a nucleophilic displacement at the 1 position of a 1-substituted-2,6-dinitro-3,4-xylene using, for example, an amine to displace a 1-chloro group.

In the process of the present invention, nitro groups are introduced ortho to an N-alkyl group of a 3,4-xylidine. This route has several unexpected advantages.

The first advantage concerns the ready availability of the starting materials. In each case, the ultimate starting material is o-xylene which is either nitrated or chlorinated. A mixture of 3-nitro-o-xylene and 4-nitro-o-xylene is produced in one case and a mixture of 3-chloro-o-xylene and 4-chloro-o-xylene is produced in the other. In the case of the nitro compounds, the ring isomers are readily separable using conventional distillation equipment while separation of 4-chloro-o-xylene from its ring isomer can only be accomplished by distillation with great difficulty owing to the closeness in the boiling points of the isomers. The second advantage in the process of the present invention is that the N-alkyl-amino substituent at the 4 position of the o-xylene ring system has been found to be strongly ortho directing with regard to nitration reactions in contrast to its 4-chloro counterpart which causes equal substitution in the meta position. This disadvantage is compounded by the fact that a portion of the 3,4-dimethyl-2,6-dinitro-chloro benzene produced forms an eutectic composition with its ring isomers so that the yield of the desired compound obtained by fractional crystallization is further reduced.

Accordingly, the novel process of the present invention concerns the preparation of compounds of the formula:

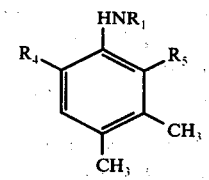

wherein $R_1$ represents a branched chain alkyl $C_4$–$C_5$ selected from the group of sec-butyl, 1-methylbutyl and 1-ethylpropyl; $R_4$ and $R_5$ are hydrogen or nitro, with the proviso that $R_4$ and $R_5$ cannot both be hydrogen, by reacting concentrated nitric acid with a compound of formula I.

Where it is desired to produce N-alkyl-2,6-dinitro-3,4-xylidines from the unnitrated xylidines, the nitration may be conducted in a single step by reacting the xylidine with 5 to 20 moles of $HNO_3$. Alternatively, it may be conducted in two steps, first forming an ortho-nitro xylidine and then nitrating it to the 2,6-dinitro compound.

The nitrations may be carried out in conventional equipment in which the novel compounds are reacted with conventional nitration reagents, such as concentrated nitric acid.

In the case of the one step dinitration of the unnitrated N-alkyl-3,4-xylidine or the mononitration of the N-alkyl-ortho-nitro-3,4-xylidine, the nitration is preferably conducted with concentrated nitric acid, optionally in solution in a solvent such as dichloroethane. The reaction is preferably carried out at low temperature usually between about −10° C. and +10° C. using a large excess of nitric acid. It is a good practice in carrying out this reaction to provide a molar ratio of acid to xylidine of about 15 to 1.

Where it is desirable to obtain the N-(alkyl)-mononitro-3,4-xylidine, the appropriate N-(alkyl)-3,4-xylidine is treated with a stoichiometric amount or slight excess of concentrated nitric acid, preferably in the presence of concentrated sulfuric acid. This reaction is preferably carried out in the presence of a solvent such as dichloroethane at a temperature between about 5° C. and 35° C. The reaction yields a mixture of the desired N-(alkyl)-2-nitro-3,4-xylidine and N-(alkyl)-6-nitro-3,4-xylidine. The mixture may be separated into its individual components by column chromatography on silica gel using hexane as the eluent. Such a separation is not necessary if it is desired to employ these compounds as intermediates for the 2,6-dinitro xylidines or where the isomer mixtures can be used in combination.

The N-alkyl-3,4-xylidines can be prepared by reacting 4-nitro-o-xylene or 3,4-xylidine (formula III) with the appropriate ketone under a hydrogen atmosphere in the presence of a conventional hydrogenation catalyst such as palladium. This reaction is depicted as follows:

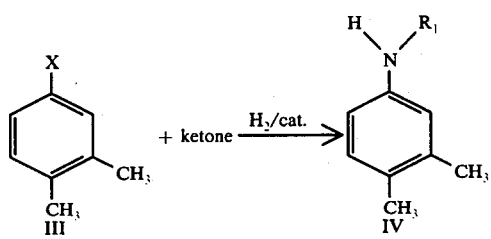

wherein X is $NH_2$ or $NO_2$; ketone is methyl ethyl ketone, methyl propyl ketone or ethyl propyl ketone; and $R_1$ is as defined for formula I above.

An alternative route to the formula IV N-(alkyl)-3,4-xylidines involves the reaction of 3,4-xylidine of formula III wherein X is $NH_2$ with one of the ketones mentioned above in the presence of an alkali metal cyanoborohydride, such as, $NaBH_3CN$. Preferably, a molecular sieve is also used to tie up the water produced by the reaction. This reaction can be carried out over a relatively wide temperature range of from about 10° C. to 70° C. and is preferably conducted in the presence of a solvent, such as a loweralkyl alcohol $C_1-C_4$.

In yet another process for the preparation of the formula IV compounds, 3,4-xylidine is treated with one of the above ketones in the presence of a molecular sieve and a solvent such as dry benzene. This reaction yields the corresponding N-(alkylidene)-3,4-xylidine which can be reduced with an alkali metal borohydride or hydrogen and a hydrogenation catalyst to yield the corresponding N-(alkyl)-3,4-xylidine.

Since the N-alkyl group in some of the xylidines contains an asymmetric carbon, optical isomerism can exist. In such case, the N-alkyl xylidines mentioned herein include the individual antimers as well as mixtures thereof.

Since resolution is an expensive and time consuming operation, it is generally preferred to employ the racemic compositions rather than the separate antimers. Where separation is desired, the N-alkyl compounds may be reacted with an optically active carboxylic acid, such as L-tartaric acid followed by separation of the diastereomers using fractional crystallization in a conventional manner.

The unexpected advantages in the way of selective herbicidal activity and low mammalian toxicity of the 2,6-dinitroxylidines produced from the novel compounds of the present invention by the nitration process of the present invention are set forth in the above-mentioned copending application. The compounds of the present invention as well as their preparation and use are further illustrated in the following examples. All parts and percentages herein are by weight unless indicated to the contrary.

EXAMPLE 1

Preparation of N-(1-Ethylpropyl)-3,4-Xylidine

4-Nitro-o-xylene (10.0 g., 0.066 mole) is shaken in a Parr hydrogenator with diethyl ketone (20 ml., 0.019 mole), 5% palladium on carbon catalyst (0.5 g.) and benzoic acid (0.5 g.) with approximately 3 atmospheres of hydrogen. When the uptake of hydrogen is complete, the suspension is filtered and analyzed by gas-liquid chromatography demonstrating thereby that N-(1-ethyl)propyl-3,4-xylidine had been produced in 83% yield.

EXAMPLE 2

Preparation of N-(1-Ethylpropyl)-3,4-Xylidine

A solution of 3,4-xylidine (1.2 g., 0.01 mole) and diethyl ketone (5 ml.) in methanol (20 ml.) is stirred at room temperature in the presence of sodium cyanoborohydride (1.1 g.) and 3A molecular sieves (3.0 g.). The pH is monitored each half hour and maintained at 6 by adding acetic acid in 5 drop portions as required. After 7 hours, the sieves are removed by filtration and the filtrate is diluted with water (100 ml.) and then acidified with hydrochloric acid. The solution is then basified with solid potassium carbonate and extracted with ethyl ether. The ether solution is dried and then evaporated leaving the desired product as a residual oil in 97.5% yield and in 93% purity as determined by gas-liquid chromatography. The compound had a boiling point of 80° C. at a pressure of 0.1 mm. Its elemental analysis is as follows:

Percentages calculated for $C_{13}H_{21}N$: C, 81.6; H, 11.1; N, 7.3. Percentages found: C, 81.4; H, 11.2; N, 7.5.

EXAMPLE 3

Preparation of N-sec-butyl-3,4-Xylidine

N-sec-butyl-3,4-xylidine was prepared by the procedure of Example 2 using an equivalent amount of methyl ethyl ketone for the diethyl ketone used therein. The desired product was obtained in a quantitative yield in 96% purity. It had a boiling point of 75°–77° C. at a pressure of 0.4 mm. and the following elemental analysis:

Percentages calculated for $C_{12}H_{19}N$: C, 81.3; H, 10.8; N, 7.9. Percentages found: C, 81.4; H, 10.8; N, 7.9.

EXAMPLE 4

Preparation of N-sec-butyl-3,4-Xylidine

Molecular sieves (Type 5A, 300 gm.) are added to 79.2 g. (1.0 mole) of methyl ethyl ketone and 121.0 g. (1.0 mole) of 3,4-dimethylaniline in 1 liter of dry benzene solvent. The reaction mixture is stirred at room temperature for 16 hours. The mixture is then filtered from the molecular sieves which are washed with dry benzene. The benzene solutions are combined and evaporated in vacuo leaving 198 g. (100%) of the desired product. The product is sensitive to hydrolysis and is therefore reduced immediately in a Parr hydrogenator using a 5% palladium on carbon catalyst to give N-sec-butyl-3,4-xylidine.

EXAMPLES 5 and 6

Preparation of N-sec-butyl-2-nitro-3,4-xylidine and N-sec-butyl-6-nitro-3,4-xylidine N-sec-butyl-3,4-xylidine (5.3 g., 0.03 mole) is dissolved in 10 ml. of dichloroethane and carefully treated with mixed acids (6 ml. concentrated sulfuric acid and 2.7 g. concentrated nitric acid) at 15°-25° C. When the addition is complete, the mixture is poured into water. The organic layer is separated and purified by column chromatography on silica gel using hexane as eluent. The first compound to elute was N-sec-butyl-2-nitro-3,4-xylidine. It was characterized by its nuclear magnetic resonance (nmr) and infrared (ir) spectra. The second compound to elute was N-sec-butyl-6-nitro-3,4-xylidine. It was characterized by its nmr and ir spectra. Analytical sample of the 6-nitro compound had a melting point of 73° C.-75° C. and the following elemental analysis:

Percentages calculated for $C_{12}H_{18}N_2O_2$: C, 64.8; H, 8.2; N, 12.6. Percentages found: C, 64.6; H, 8.2; N, 12.6.

EXAMPLES 7 and 8

Preparation of N-(1-Ethylpropyl)-2-nitro-3,4-xylidine and N-(1-Ethylpropyl)-6-nitro-3,4-xylidine The above compounds were prepared and isolated by the procedure of Examples 5 and 6 substituting an equivalent amount of N-(1-ethylpropyl)-3,4-xylidine for the N-sec-butyl-3,4-xylidine used therein.

The 6-nitro compound after recrystallization from methanol had a melting point of 58° C.-60° C. and the following elemental analysis:

Percentages calculated for $C_{13}H_{20}N_2O_2$: C, 66.1; H, 8.5; N, 11.9. Percentages found: C, 66.1; H, 8.6; N, 11.7.

The 2-nitro compound after purification by chromatography is an oil. It had the following elemental analysis:

Percentages calculated for: $C_{13}H_{20}N_2O_2$: C, 66.1; H, 8.5; N, 11.9. Percentages found: C, 67.7; H, 8.9; N, 12.0.

The 6-nitro compound is alternatively prepared by reacting 3.8 g. (0.02 mole) of N-1-(ethylpropyl)-3,4-xylidine and 5.0 ml. (0.08 mole) of 70% concentrated nitric acid as described in Example 12 below. The desired product is isolated in a conventional manner by chromatography on silica gel.

EXAMPLES 9-11

The selective preemergence herbicidal activity of the compounds of the invention is exemplified by the following tests in which the seeds of a variety of monocotyledonous and dicotyledonous plants are separately mixed with potting soil and a ½ inch layer of this seed-soil mix is placed on top of approximately 1½ inches of potting soil in separate 2½ × 2½ inch plastic pots. After planting, the cups are sprayed with the selected aqueous-acetone solution containing test compound in sufficient quantity to provide the equivalent of 0.06 to 10 pounds per acre of test compound per cup. The treated cups are then placed on greenhouse benches, watered and cared for in accordance with greenhouse procedures. Three or four weeks after treatment, the tests are terminated and each cup is examined and rated according to the rating system set forth below. The results are set forth in Table I below.

| Rating System | % Difference in Growth from the Cneck[1] |
|---|---|
| 0 - no effect | 0 |
| 1 - possible effect | 1 - 10 |
| 2 - slight effect | 11 - 25 |
| 3 - moderate effect | 26 - 40 |
| 5 - definite injury | 41 - 60 |
| 6 - herbicidal effect | 61 - 75 |
| 7 - good herbicidal effect | 76 - 90 |
| 8 - approaching complete kill | 91 - 99 |
| 9 - complete kill | 100 |
| 4 - abnormal growth, i.e., a definite physiological malformation but with an over-all effect less than a 5 on the rating scale. | |
| 1 - Based on visual determination of stand, size, vigor, chloresis, growth malformation and over-all plant appearance. | |

PLANT ABBREVIATIONS

CR — Crabgrass (Digitaria sanguinalis)
PI — Pigweed (Amaranthus retroflexus)
LA — Lambsquarters (Chenopodium album)
COR — Corn (Zea mays)
WO — Wild Oats (Avena fatua)
MU — Mustard (Brassica kaber)
RAG — Ragweed (Ambrosia artemisiifolia)
BA — Barnyardgrass (Echinochloa crusgalli)
GRF — Green Foxtail (Setaria viridis)
MG — Annual Morningglory (Itomoea purturea and Itomoea hederacea)
COT — Cotton (Gossypium hirsutum)
SB — Sugarbeets (Beta bulugaris)
SOY — Soybean (Glyzine max)

TABLE I

| | | | Preemergence Herbicidal Activity | | | | | | | | | | | | |
|---|---|---|---|---|---|---|---|---|---|---|---|---|---|---|---|
| | Active Ingredient | Rate of Application | Plants | | | | | | | | | | | | |
| Ex. No. | Structure | Treatment lb./Acre | Annual Weeds | | | | | | | | | Crops | | | |
| | | | LA | MU | PI | RAG | MG | BA | CR | GRF | WO | COR | COT | SOY | SB |
| 9 | HNCH(C₂H₅)₂ on O₂N-xylene ring with CH₃, CH₃ | 4 | 5 | | 6 | 2 | 9 | 9 | 9 | 2 | 0 | 2 | 0 | 0 | |
| | | 2 | 8 | | 5 | 0 | 8 | 9 | 9 | 0 | 0 | 0 | 0 | 0 | |
| | | 1 | 0 | | 3 | 0 | 7 | 9 | 9 | 0 | 0 | 0 | 0 | 0 | |

TABLE I-continued

| | | | Preemergence Herbicidal Activity | | | | | | | | | | | | |
|---|---|---|---|---|---|---|---|---|---|---|---|---|---|---|---|
| | Active Ingredient | Rate of Application | Plants | | | | | | | | | | | | |
| Ex. No. | Structure | Treatment lb./Acre | Annual Weeds | | | | | | | | | Crops | | | |
| | | | LA | MU | PI | RAG | MG | BA | CR | GRF | WO | COR | COT | SOY | SB |
| 10 | HNCH(C₂H₅)₂ on benzene ring with NO₂, CH₃, CH₃ substituents | 10 | 8 | 0 | 9 | 0 | 0 | 9 | 9 | 9 | 9 | | | | |
| | | 2 | 3 | | 6 | | 0 | 9 | 9 | 9 | 5 | 2 | 0 | 0 | 2 |
| | | 1 | 0 | | 3 | | 0 | 8 | 9 | 8 | 3 | 0 | 0 | 0 | 0 |
| 11 | O₂N-benzene with HNCH(CH₃)(C₂H₅), CH₃, CH₃ substituents | 2 | 0 | | 0 | | 0 | 3 | 9 | 7 | 0 | 0 | 0 | 0 | 0 |
| | | 1 | 0 | | 0 | | 0 | 3 | 8 | 5 | 0 | 0 | 0 | 0 | 0 |

EXAMPLES 12–25

The process of converting the compounds of the present invention to 2,6-dinitroanilines is demonstrated in Examples 12–16. The utility of the products so produced is demonstrated in comparative Examples 17–25.

EXAMPLE 12

Preparation of N-sec-Butyl-2,6-dinitro-3,4-xylidine

N-sec-butyl-3,4-xylidine (1.2 g., 6.7 × 10⁻³ mole) is added to 70% nitric acid (13 ml.) at 15° C. After one hour the reaction mixture is poured into ice water and extracted with ethyl ether. The extract is dried over MgSO₄ and evaporated in vacuo leaving the desired product as 1.55 g. of solid residue. The product is purified by chromatography on silica gel using hexane as eluent. The total weight of purified product obtained is 1.1 g. (60%) and has a melting point of 41°–45° C. Recrystallization from hexane gives the analytical sample with a melting point of 43° C.–44° C. and an elemental analysis of:

Percentages calculated for $C_{12}H_{17}N_3O_4$: C, 53.9; H, 6.4; N, 15.7. Percentages found: C, 54.0; H, 6.2; N, 15.7.

EXAMPLE 13

Preparation of N-(1-Ethylpropyl)-2,6-dinitro-3,4-xylidine

The subject compound is prepared by the procedure of Example 12 substituting an equivalent amount of N-(1-ethyl-propyl)-3,4-xylidine for the N-sec-butyl-3,4-xylidine used therein. The desired product is produced in an 80% yield. Purification is effected by recrystallization in methanol to produce a crystalline produce having a melting point of 56° C.–57° C. and the following elemental analysis:

Percentages calculated for $C_{13}H_{19}N_3O_4$: C, 55.5; H, 6.8; N, 14.9. Percentages found: C, 55.4; H, 6.8; N, 15.0.

EXAMPLE 14

Preparation of N-(1-Ethylpropyl)-2,6-dinitro-3,4-xylidine

N-(1-ethylpropyl)-2-nitro-3,4-xylidine (1.0 g., 4 × 10⁻³ mole) is added to 10 ml. HNO₃ (70% concentration). After 90 minutes the reaction mixture is worked up as described in Example 12 to give a 100% crude yield of the desired dinitro product. Gas-liquid chromatography shows this product to be 97% pure.

EXAMPLE 15

Preparation of N-(1-Ethylpropyl)-2,6-dinitro-3,4-xylidine

The subject compound is produced in 90% crude yield by the procedure of Example 14, substituting an equivalent amount of N-(1-ethylpropyl)-6-nitro-3,4-xylidine for the 2-nitro compound used therein. This produce had a 90% purity.

EXAMPLE 16

41.0 g. (0.214 mole) of N-3-pentyl-3,4-dimethylaniline and 128 ml. of 1,2-dichloroethane are charged to a flask. The solution is stirred and cooled to 0°–5° C. 254 g. (3.22 mole) of 80% HNO₃ is added at 0°–5° C. over a period of 135 minutes. After the addition, the reaction mixture is held at 0°–5° C. for 240 minutes. At the end of the hold period, the cold reaction mixture is poured onto 254 g. of ice. 128 ml. of ClCH₂CH₂Cl is added. After removing the aqueous phase, the product solution is washed with 5% aqueous bicarbonate and water. The crude product is obtained by drying the organic layer over anhydrous MgSO₄, filtering and removing the solvent from the filtrate at reduced pressure. 52.3 g. of crude product assaying 89.7% yield is obtained. The real yield is 79.3%. The product crystallize during storage at ambient conditions.

EXAMPLES 17–25

The selective preemergence herbicidal activity of the compounds of the invention is exemplified by the following tests in which the seeds of a variety of monocotyledonous and dicotyledonous plants are separately mixed with potting soil and a ½ inch layer of this seed-soil mix is placed on top of approximately 1½ inch of potting soil in separate 2½ × 2½ inch plastic pots. After planting, the cups are sprayed with the selected aqueous-acetone solution containing test compound in sufficient quantity to provide the equivalent of 0.06 to 10 pounds per acre of test compound per cup. The treated cups are then placed on greenhouse benches, watered and cared for in accordance with greenhouse procedures. Three or four weeks after treatment, the tests are terminated and each cup is examined and rated according to the rating system above. The results of these tests set forth in Table II show the herbicidal utility of the products produced by the process of the present invention and demonstrate the exceptional activity of N-sec-butyl-2,6-dinitro-3,4-xylidine; N-(1-ethylpropyl)-2,6-dinitro-3,4-xylidine and N-(1-methylbutyl)-2,6-dinitro-3,4-xylidine and the virtual ineffectiveness of the closely related homologues thereof when used at equivalent rates or a twofold increase in rate.

TABLE II

| | | Preemergence Herbicidal Activity | | | | | | | | | | | | | |
|---|---|---|---|---|---|---|---|---|---|---|---|---|---|---|---|
| | | Rate of Application Treatment | Plants | | | | | | | | | | | | |
| | | | Annual Weeds | | | | | | | | | Crops | | | |
| Ex. No. | Active Ingredient Structure | lb./Acre | LA | MU | PI | RAG | MG | BA | CR | GRF | WO | COR | COT | SOY | SB |
| 17 | HN—CH(C$_2$H$_5$)$_2$ on 2,6-dinitro-3,4-xylidine ring | 0.5 | 7 | 8 | | 6 | 9 | 9 | 9 | 7 | 5 | 0 | 0 | 3 | |
| | | 0.25 | 6 | 7 | | 4 | 9 | 9 | 9 | 3 | 0 | 0 | 0 | 3 | |
| | | 0.13 | 6 | 3 | | 2 | 7 | 9 | 9 | 3 | 0 | 0 | 0 | 0 | |
| | | 0.06 | 5 | 3 | | 2 | 6 | 8 | 8 | 0 | 0 | 0 | 0 | 0 | |
| 18 | N—CH(CH$_3$)(C$_2$H$_5$) on 2,6-dinitro-3,4-xylidine ring | 1 | 8 | 5 | | 0 | 8 | 9 | 8 | 1 | 0 | 0 | 0 | 0 | |
| | | 0.5 | 7 | 0 | | 0 | 8 | 9 | 9 | 0 | 0 | 0 | 0 | 0 | |
| | | 0.25 | 6 | 0 | | 0 | 3 | 9 | 8 | 0 | 0 | 0 | 0 | 0 | |
| 19 | HNCH(CH$_3$)(C$_3$H$_7$) on 2,6-dinitro-3,4-xylidine ring | 1 | 7 | 7 | | 0 | 9 | 9 | 9 | 1 | 5 | 0 | 1 | 5 | |
| | | 0.5 | 7 | 5 | | 0 | 8 | 9 | 9 | 0 | 0 | 0 | 0 | 0 | |
| | | 0.25 | 5 | 0 | | 0 | 7 | 7 | 6 | 0 | 0 | 0 | 0 | 0 | |
| 20 | NH—C$_4$H$_9$-n on 2,6-dinitro-3,4-xylidine ring | 1 | 0 | 0 | | 0 | 0 | 7 | 2 | 0 | 0 | 0 | 0 | 0 | |
| | | 0.5 | 0 | 0 | | 0 | 0 | 7 | 1 | 0 | 0 | 0 | 0 | 0 | |
| | | 0.25 | 0 | 0 | | 0 | 0 | 0 | 0 | 0 | 0 | 0 | 0 | 0 | |
| 21 | HN—C$_4$H$_9$-iso on 2,6-dinitro-3,4-xylidine ring | 1 | 0 | 0 | | 0 | 3 | 7 | 5 | 0 | 0 | 0 | 0 | 0 | |
| | | 0.5 | 0 | 0 | | 0 | 1 | 3 | 2 | 0 | 0 | 0 | 0 | 0 | |
| | | 0.25 | 0 | 0 | | 0 | 0 | 0 | 0 | 0 | 0 | 0 | 0 | 0 | |
| 22 | HNCH$_2$CH$_2$CH(CH$_3$)$_2$ on 2,6-dinitro-3,4-xylidine ring | 1 | 0 | 0 | | 0 | 0 | 7 | 0 | 0 | 0 | 0 | 0 | 0 | |
| | | 0.5 | 0 | 0 | | 0 | 0 | 2 | 0 | 0 | 0 | 0 | 0 | 0 | |
| 23 | HN—CH(CH$_3$)—C$_4$H$_9$-tert on 2,6-dinitro-3,4-xylidine ring | 1 | 0 | 0 | | 0 | 0 | 0 | 0 | 0 | 0 | 0 | 0 | 0 | |
| | | 0.5 | 0 | 0 | | 0 | 0 | 0 | 0 | 0 | 0 | 0 | 0 | 0 | |

TABLE II-continued
| Ex. No. | Active Ingredient Structure | Rate of Application Treatment lb./Acre | Preemergence Herbicidal Activity Plants | | | | | | | | | | | | |
|---|---|---|---|---|---|---|---|---|---|---|---|---|---|---|
| | | | Annual Weeds | | | | | | | | | Crops | | | |
| | | | LA | MU | PI | RAG | MG | BA | CR | GRF | WO | COR | COT | SOY | SB |
| 24 | 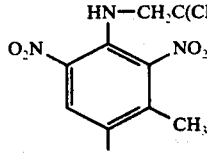 | 2 | 0 | 0 | 0 | 0 | 0 | 0 | 3 | 0 | 0 | 0 | 0 | 0 | 0 |
| | | 1 | 0 | 0 | 0 | 0 | 0 | 0 | 0 | 0 | 0 | 0 | 0 | 0 | 0 |
| 25 | 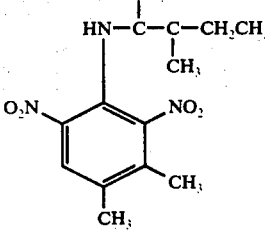 | 1 | 3 | | 3 | 0 | | 0 | 7 | 0 | 0 | 0 | 0 | 0 | 2 |
| | | 5 | 0 | | 0 | 0 | | 0 | 2 | 0 | 0 | 0 | 0 | 0 | 0 |
We claim:
1. A compound selected from the group consisting of N-sec-butyl-6-nitro-3,4-xylidine; N-(1-ethylpropyl)-2-nitro-3,4-xylidine; and N-(1-ethylpropyl)-6-nitro-3,4-xylidine.
* * * * *